(12) United States Patent
Lichtman (10) Patent No.: US 6,292,221 B1
(45) Date of Patent: Sep. 18, 2001

(54) MOTORIZED FOCUSING DEVICE AND VIEWING SYSTEM UTILIZING SAME

(75) Inventor: Philip R. Lichtman, Newton, MA (US)

(73) Assignee: Vista Medical Technologies, Inc., Carlsbad, CA (US)

( * ) Notice: Subject to any disclaimer, the term of this patent is extended or adjusted under 35 U.S.C. 154(b) by 0 days.

(21) Appl. No.: 09/193,597

(22) Filed: Nov. 17, 1998

(51) Int. Cl.[7] ............... G03B 13/00; A61B 1/04; A61B 1/06; G02B 15/14; G02B 7/02
(52) U.S. Cl. ............... 348/345; 600/112; 600/167; 359/696; 359/823
(58) Field of Search ............... 348/65, 345; 359/696, 359/822, 823; 600/112, 118, 163, 167

(56) References Cited

U.S. PATENT DOCUMENTS

| | | | |
|---|---|---|---|
| 3,967,056 | * 6/1976 | Yata et al. | 348/356 |
| 4,445,757 | * 5/1984 | Enomoto et al. | 359/823 |
| 4,609,260 | * 9/1986 | Kawai | 359/705 |
| 4,905,668 | * 3/1990 | Oshawa | 348/65 |
| 5,008,534 | * 4/1991 | Yonezawa et al. | 250/229 |
| 5,056,902 | 10/1991 | Chinnock et al. | 359/503 |
| 5,212,595 | * 5/1993 | Dennison, Jr. et al. | 359/823 |
| 5,359,992 | 11/1994 | Hori et al. | 128/4 |
| 5,682,199 | 10/1997 | Lankford | 348/72 |
| 5,701,206 | * 12/1997 | Sasaki et al. | 359/823 |
| 5,808,813 | * 9/1998 | Lucey et al. | 348/65 |
| 5,911,088 | * 6/1999 | Higashihara et al. | 396/387 |

* cited by examiner

Primary Examiner—Andrew B. Christensen
(74) Attorney, Agent, or Firm—Pandiscio & Pandiscio (57) ABSTRACT

An improved focusing coupler device for coupling the image capturing portion of an endoscope to a video camera is disclosed. The coupler device includes a housing having an elongate internal chamber defining an optical pathway for connecting the optical image paths of the endoscope and the camera, first and second windows closing off the opposite ends of the chamber, a lens transport assembly disposed in the chamber for relative movement between the ends of the chamber, the lens transport assembly comprising a lens carrier that defines a longitudinal series of rack gear teeth and is movable between the opposite ends of the chamber, and at least one focusing lens mounted to the lens carrier in coaxial alignment with the longitudinal axis of the chamber. The housing also includes a cavity containing a drive device and a passageway communicating with the midsection of the chamber and the distal end of the cavity chamber, and gear means for connecting the rack gear teeth to the drive device so as to translate rotational movement of the drive shaft in the cavity through the passageway to the rack gear teeth and thereby to selectively longitudinally move the lens transport assembly in the chamber.

2 Claims, 7 Drawing Sheets

MOTORIZED FOCUSING DEVICE AND VIEWING SYSTEM UTILIZING SAME

BACKGROUND

1. Field of Invention

The present invention generally relates to optical devices wherein one or more movable lenses are provided for focusing an image of an object in a preselected plane. More particularly, the invention relates to an improved focusing coupler capable of varying the field of view and magnification, and to a viewing system utilizing the same, for use by surgeons in endoscopically viewing internal, "closed", surgical sites.

2. Summary of the Prior Art

Endoscopes are medical devices which are used to provide external images of organs and structures within a human or animal. As used herein, the term "endoscope" includes, but is not limited to, arthroscopes, colonoscopes, bronchoscopes, hysteroscopes, cystoscopes, sigmoidoscopes, laparoscopes and urethrascopes.

Typically, endoscopes comprise an insertion portion in the form of a hollow shaft that is designed for insertion through a body orifice or a small incision into an internal body cavity. An objective lens unit consisting of one or more lenses is mounted within the shaft at its forward (distal) end. The objective lens unit forms an image of the area that is viewed by it, i.e., the "target". The image of the target so captured is then transmitted to an optical viewing device or to an electronic imaging device. The hollow shaft may, but need not, include optical image transmission apparatus, e.g., a relay lens, for applying the image to the optical viewing device or to the electronic imaging device.

A conventional optical endoscope provides an optical viewing capability in the form of an eyepiece unit that is affixed to the proximal (rear) end of the shaft. The eyepiece unit is nominally focused to infinity for direct viewing of the image by the surgeon. More specifically, the objective lens unit of a conventional optical endoscope is usually designed so as to form a focused image of an object or other target located at a predetermined target distance therefrom. That predetermined object distance is the object position relative to the objective lens unit which is thought by the designer to be most frequently required by a surgeon. Further, the overall optics system of a conventional optical endoscope is designed so that the image beam emerging from the eyepiece unit is collimated, i.e., focused nominally to infinity. The cornea of the surgeon's eye acts to focus the collimated image beam on the retina of the surgeon's eye during direct viewing of the image by the surgeon.

Another type of endoscope is an integrated video endoscope that incorporates a video camera. As used herein, the term "video camera" is used to designate a solid state, electronic imaging device, preferably in the form of a charge coupled device ("CCD"). More particularly, in the typical integrated video endoscope, the CCD or other solid state imaging device is mounted within the hollow endoscope shaft, or in a housing that is attached to the proximal end of the hollow shaft. The electronic imaging device generates electrical signals representative of the images received from the objective lens unit. Those signals then are processed to generate video signals which are used to create a video display on a conventional TV monitor or a head-mounted video display unit. In this connection, it should be noted that in addition to the CCD or other electronic imaging device, the camera may comprise one or more circuits for controlling the operation of the CCD and processing the CCD's output signals.

It also should be noted that many endoscopes are known which have stereoscopic capabilities. In such endoscopes, the optics are designed so as to generate first and second images of the target, with each image being taken from a different angle. The two images either may be viewed directly by a stereo (binocular) eyepiece unit, or they may be transmitted to an electronic imaging device for generating signals that in turn are used to generate a stereoscopic video display according to known techniques. The depth perception provided by such electronically generated stereo images is valuable to a surgeon in conducting a surgical procedure within a "closed" surgical site.

The present state of the art regarding endoscopic systems is exemplified by the teachings and disclosures of the following United States patents and patent applications: U.S. patent. application Ser. No. 08/722,724 filed Oct. 1, 1996 by K Hori et al; U.S. Pat. No. 5,538,497 issued Jul. 23, 1996 to K Hori; U.S. Pat. No. 5,582,576 issued Dec. 10, 1996 to K. Hori et al.; U.S. Pat. No. 5,603,687 issued Feb. 18, 1997 to K. Hori et al.; U.S. Pat. No. 5,662,584 issued Sep. 2, 1997 to K. Hori et al.; U.S. Pat. No. 5,682,199 issued Oct. 28, 1997 to James D. Lankford; U.S. Pat. Nos. 5,673,147, 5,191,203, and 5,122,650, all issued to Harry R. McKinley; and U.S. Pat. No. 5,612,816, issued to Fritz Strahle; and the art cited during the prosecutions of those patents and applications The disclosures and teachings of the above-identified prior art are hereby incorporated by reference into this specification.

A conventional optical endoscope, whether monocular or stereo, may be converted to a video endoscope by attaching a video camera head to the endoscope in a position to receive the image beams passed by the eyepiece unit (as used herein the term "video camera head" designates a housing that contains a video camera and that is adapted to be connected to an endoscope directly or via an endoscope coupler). Such conversions are favored in the art. This is because a single video camera head may be used with many different endoscopes, thereby providing significant cost savings over the alternative of providing an integrated video endoscope for each type of surgical procedure. However, since the exit image beam of the conventional eyepiece unit is generally collimated, and since the target distance will vary as the endoscope is manipulated by the surgeon, it is desirable to provide a focusing device between the video camera head and the conventional optical endoscope so that the image beam passed by the eyepiece unit can be focused so as to accommodate a wide range of object distances. The use of such a focusing device has the effect of changing the magnification, and hence the field of view, of the image, while keeping the image properly focused on the camera image plane or the surgeon's retina.

Heretofore, focusing couplers have been available which include a focusing lens unit mounted for reciprocal movement within a coupler housing, and a manually movable actuating means located outside of the housing which is mechanically or magnetically coupled to the focusing lens unit for moving that unit so as to focus the image beam on the image plane of the CCD or other electronic imaging device of a video camera. Examples of such prior art couplers are provided by U.S. Pat. No. 5,359,992, issued Nov. 1, 1994 to K. Hori et al and U.S. Pat. No. 5,056,902, issued Oct. 15, 1991 to R. B. Chinnock et al, and the prior art listed in those patents.

All such externally operable focusing couplers provided for use with conventional optical endoscopes are characterized by several disadvantages. For example, to the extent that such focusing couplers involve externally movable elements having closely fitting surfaces, such as manually rotatable focusing rings, the areas between the closely fitting surfaces provide small volumes into which micro-organisms can enter. These small volumes are often referred to in the art as "bug traps", and are to be avoided whenever possible because they present sterilization problems. Also, such manually focused devices require the use of a surgeon's hand, which in turn may require the surgeon to divert his attention from the surgical procedure being performed and/or the video display of the surgical site. Further, manually operable focusing couplers are not adapted for use with autofocusing controls.

SUMMARY OF THE INVENTION

Accordingly, it is an object of the present invention to provide an improved focusing coupler for endoscopes which has no external close fitting surfaces constituting so-called "bug traps" which make it difficult to attain complete sterilization of the device.

Another object of the present invention to provide an improved endoscope focusing coupler which is (i) simple in construction; (ii) easy to use; (iii) capable of sensitive adjustment; and (iv) readily sterilizable by any of the common and widely available sterilization modalities, such as steam autoclaving, immersion in a sterilizing liquid, and gas sterilization.

A further object of the present invention is to provide an endoscope focusing coupler which may be operated by a surgeon without requiring the use of his hands or the diversion of his attention from the surgical procedure being performed and/or the surgical site image provided by the imaging device.

Still another object of the present invention is to provide a novel focusing coupler that can be quickly and easily inserted between, and coupled to, a conventional optical endoscope and a video camera head.

A further object of the present invention is to provide an improved endoscope/video camera system that utilizes a motorized optical focusing device for sharply focusing images from a conventional optical endoscope onto the imaging plane of a video camera.

Yet another object of the present invention is to provide a motorized focusing coupler for use between a conventional optical endoscope and a video camera head for maintaining the focus of the image presented to the video camera as the object distance is varied.

A further object is to provide a motorized focusing device that can be embodied in or coupled to a conventional optical endoscope.

These and other objects are accomplished by a motorized focusing coupler made and used in accordance with this invention. The preferred embodiment of the focusing coupler includes a housing, a focusing lens transport assembly movably mounted within the housing, an electrical motor, and gear means driven by the motor for mechanically moving the lens transport assembly in the housing so as to provide an image beam focus adjustment.

The housing comprises a bore that forms a chamber in which the lens transport assembly is movably disposed, and transparent members closing off the ends of the bore. The lens transport assembly comprises a hollow lens carrier and at least one focusing lens mounted coaxially therein. The lens carrier also defines a longitudinal series of rack gear teeth on its outer surface. The housing is also provided with a motor-receiving chamber and a cavity forming a passageway between the motor-receiving chamber and the bore to accommodate gear means for moving the lens transport assembly. A biasing means, typically in the form of a compression coil spring, is disposed within the bore for urging the lens transport assembly in a first direction in the bore.

The motor means is of the reversible drive type and the gear means includes a gear on the output shaft of the motor and a series of gear teeth on the outer surface of the lens carrier. In one preferred embodiment, the gear means comprises a worm gear affixed to the output shaft of the motor and a helical pinion gear that couples the worm gear to gear teeth on the outer surface of the lens carrier. Alternatively, the worm gear may engage the gear teeth on the lens carrier directly. Operation of the motor causes the gear means to move the lens carrier lengthwise in the bore between a proximal-most position and a distal-most position therein.

The invention also takes the form of a viewing system for an endoscope, with the system comprising a motorized focusing device as herein described and illustrated, attachment means for attaching the housing of the focusing device to the optical viewing device of a conventional optical endoscope, and a video camera for acquiring images passed by the focusing device and generating output electrical signals representative of said images.

In an alternate embodiment of the invention, the housing for the focusing device also contains the video camera.

BRIEF DESCRIPTION OF THE DRAWINGS

These and other features and advantages of the invention will become apparent to those skilled in the art from the following detailed description of the preferred embodiments thereof in conjunction with the appended drawings, wherein like reference numerals are used to refer to like elements throughout, and wherein.

DETAILED DESCRIPTION OF PREFERRED EMBODIMENT

Referring now to the appended drawings, and particularly to FIGS. 1–5, there is shown a preferred embodiment of the motorized focusing coupler of the present invention. This coupler is designed for insertion into an optical path extending between a conventional optical endoscope and an imaging device in the form of a video camera head, as discussed hereinafter in greater detail.

Figure 1:
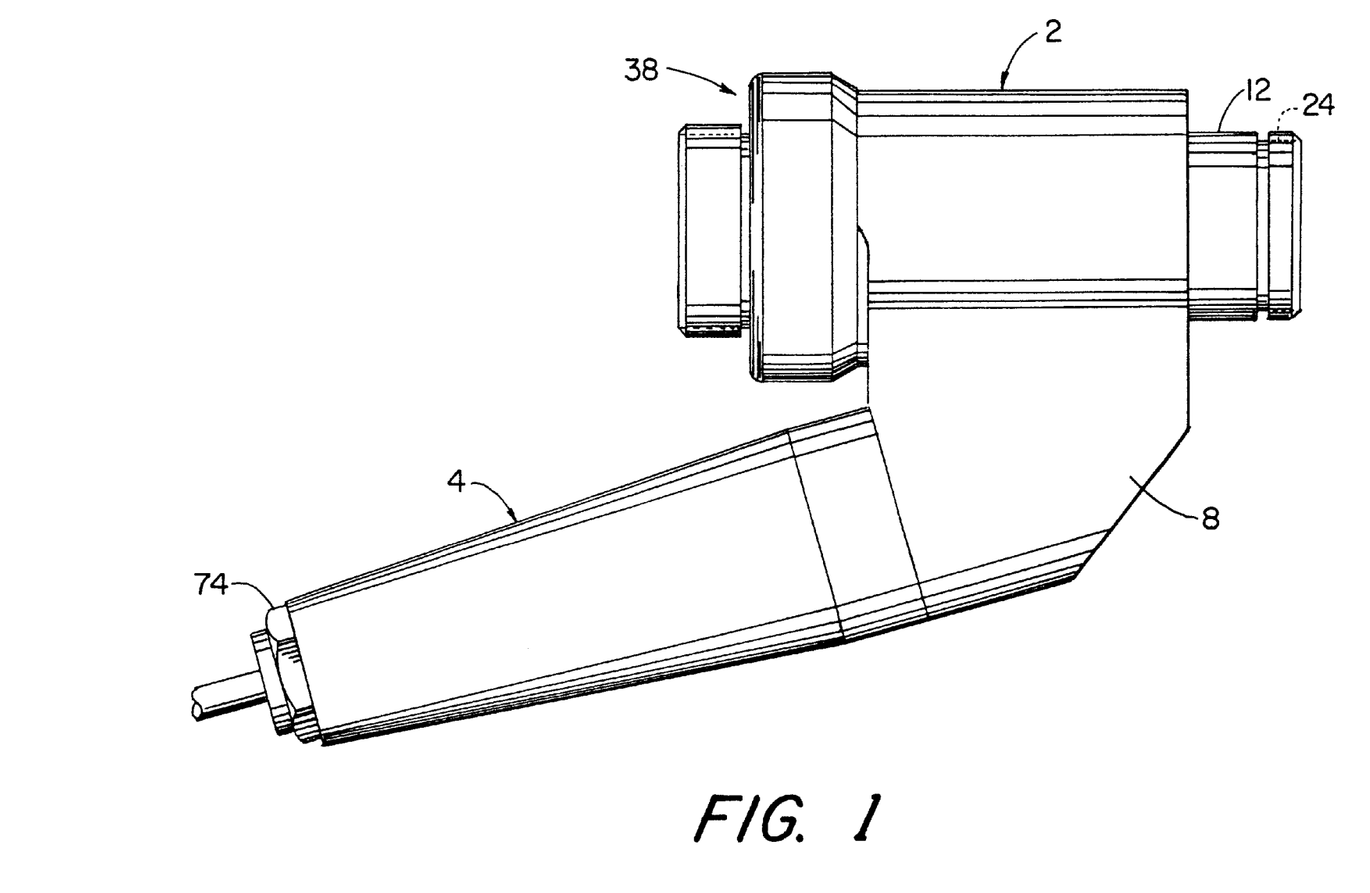
FIG. 1 is a right side elevational view of a representative motorized focusing coupler in accordance with the present invention.
Figure 2:
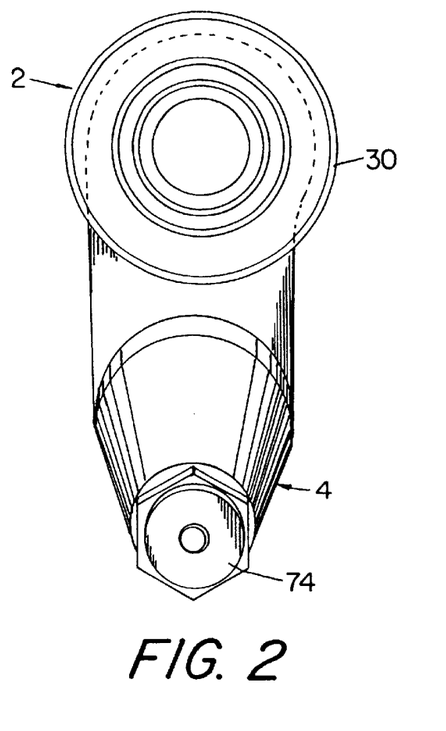
FIG. 2 is a proximal end elevational view of the motorized focusing coupler depicted in FIG. 1.
Figure 3:
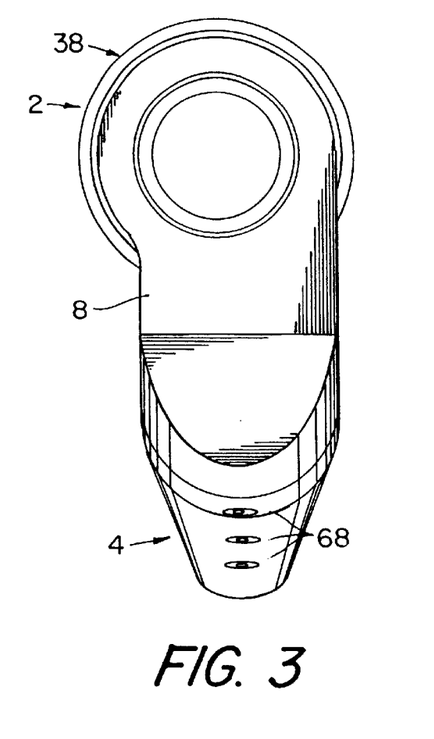
FIG. 3 is a distal end elevational view of the motorized focusing coupler depicted in FIG. 1.
Figure 4:
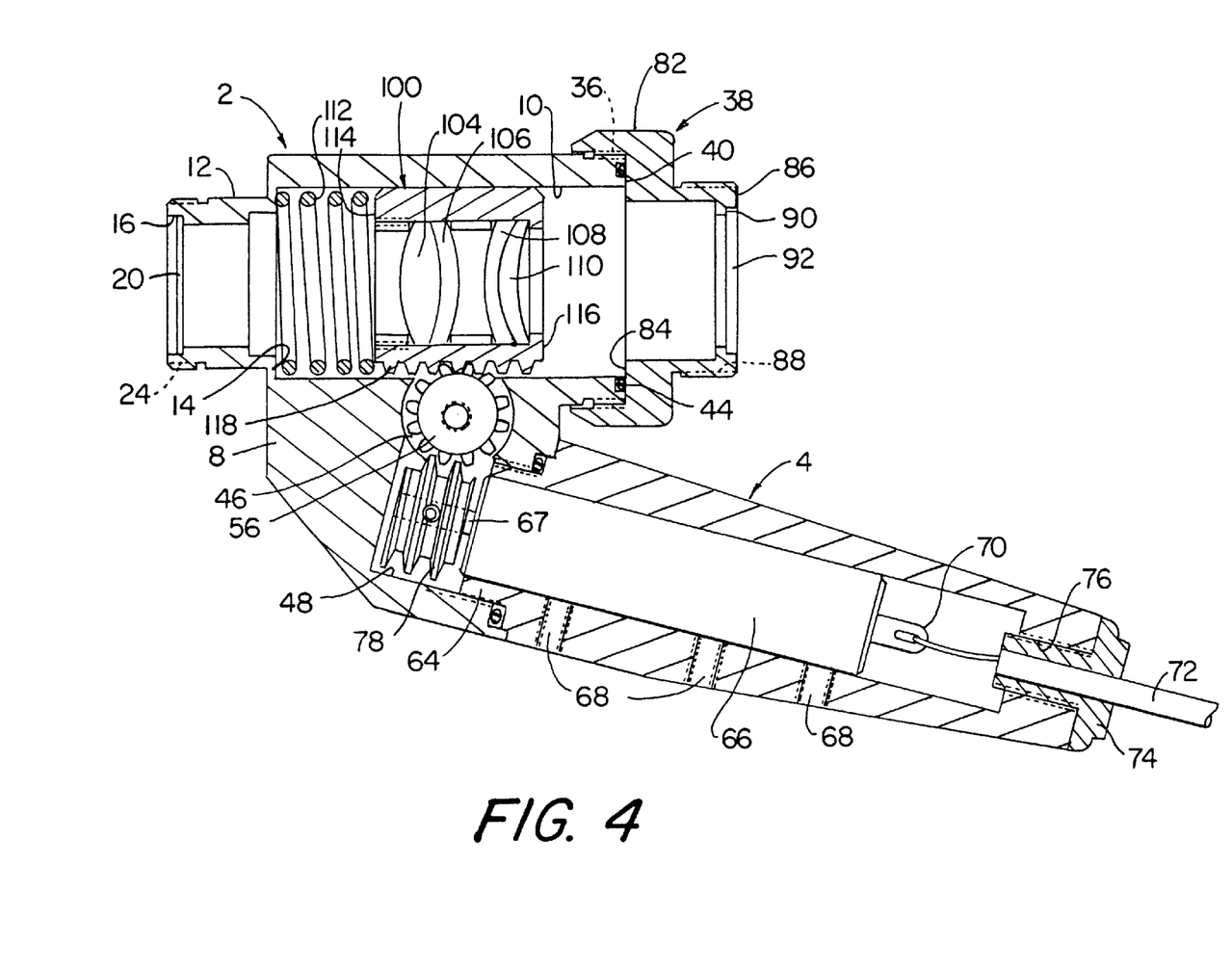
FIG. 4 is a left side, sectional, elevational view of the motorized focusing coupler depicted in FIG. 1, showing the lens transport assembly located in a position between its distal-most position and its proximal-most position in the bore.
Figure 7:
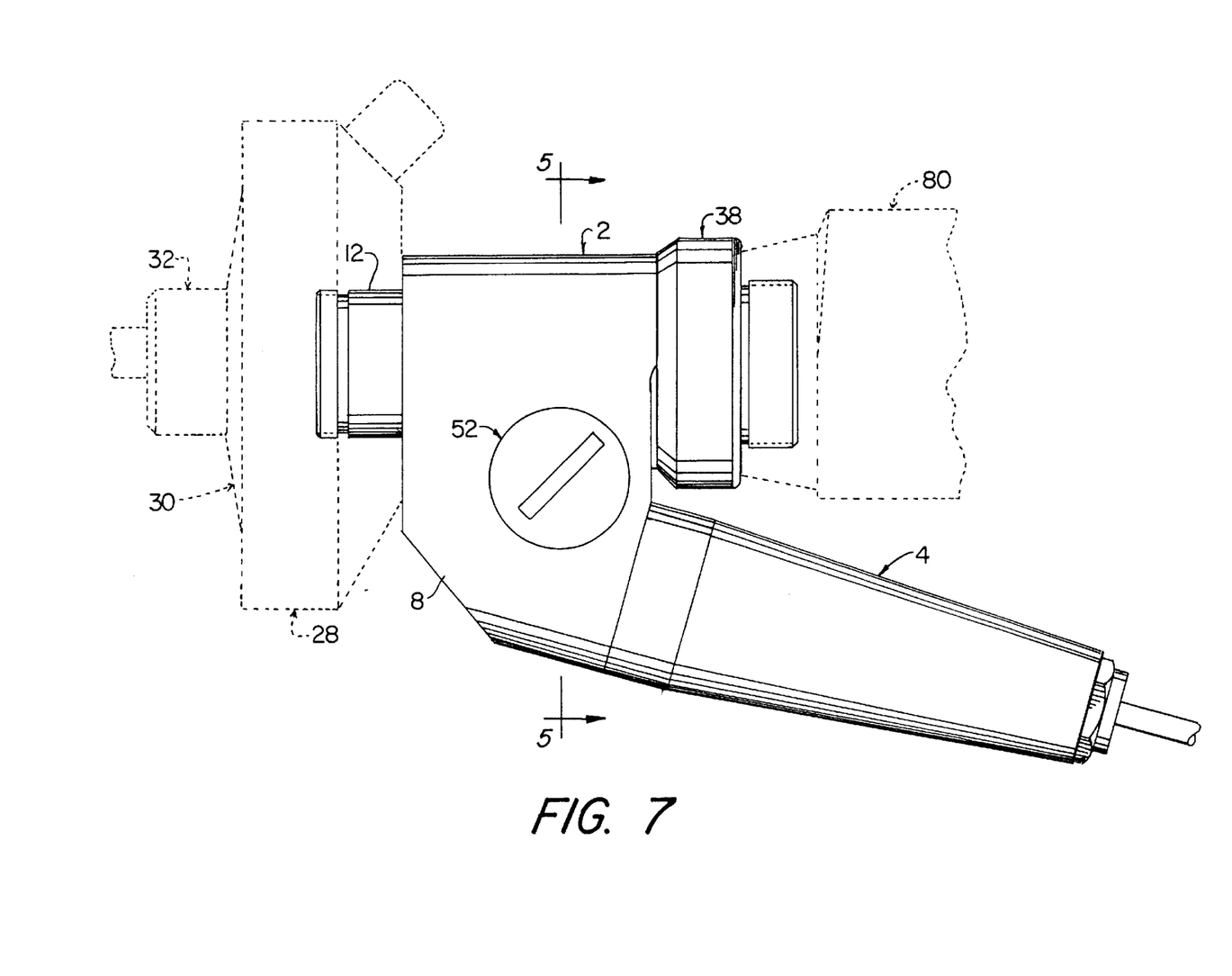
FIG. 7 is a left side elevational view of the motorized focusing coupler depicted in FIG. 1, showing in phantom (i) a conventional optical endoscope and coupler attached to its distal end and (ii) a video camera head attached to its proximal end.

As seen best in FIGS. 1, 4 and 7, the coupler comprises a housing assembly in the form of a main housing 2 and a motor support housing 4. Main housing 2 is formed with a lateral extension 8 to which motor support housing 4 is attached, and also with a cylindrical bore 10 of substantially constant diameter. Housing 2 also has a hollow cylindrical extension 12 (FIG. 4) at its distal end which is coaxial with bore 10. The inner diameter of the distal end of bore 10 is reduced in diameter, thereby forming an annular proximally-facing shoulder 14 which functions as a spring stop as described hereinafter.

As seen in FIG. 4, the open distal end of cylindrical extension 12 has a stepped annular recess 16 in which is positioned a window 20 of glass or some other transparent material. Window 20 is secured in place, e.g., by a cement, so as to make an hermetic seal with extension 12. Referring to FIGS. 1, 4 and 7, the outer surface of the end portion of cylindrical extension 12 is provided with a screw thread 24 which is used to releasably attach cylindrical extension 12 to an endoscope holder 28 (sometimes called an "endoscope coupler") which is releasably attached to the eyepiece 30 of an optical endoscope 32 (all as shown in phantom in FIG. 7). Holder 28 supports the endoscope 32. When the focusing coupler housing 2 is attached to the endoscope 32 via the holder 28, the center axes of extension 12 and bore 10 are aligned with the optical axis of the endoscope 32. The proximal end of housing 2 has an external screw thread 36 (FIG. 4) for mating with an adaptor 38, which will be described in greater detail below. The flat proximal end surface 40 of housing 2 has a circular groove which contains an elastomeric O-ring sealing member 44.

Figure 5:
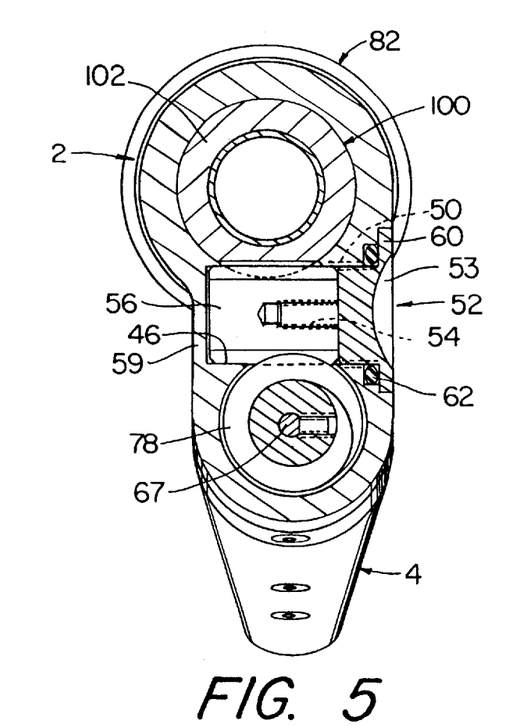
FIG. 5 is a cross-sectional view of the motorized focusing coupler depicted in FIG. 1 taken along the line 5—5 of FIG. 7.

Referring to FIGS. 4 and 5, the lateral extension 8 of housing 2 has a transversely-extending cavity 46 that intersects bore 10 at the six o'clock position, plus an inclined bore 48 that intersects cavity 46 and is open at its outer end so as to communicate with the interior of motor support housing 4.

Cavity 46 is a blind cylindrical bore that is provided with an internal screw thread 50 at its open end for the purpose of making a screw connection with a threaded plug 52. A pinion gear 56 is disposed in cavity 46. The outer diameter of pinion gear 56, i.e., the diameter at the tips of its teeth 57, is sized so that the gear makes a close but rotating fit in bore 46. Plug 52 has a flange 60 that is received in a circular surface groove in housing 2 and engages an O-ring 62 held in a second groove in housing 2, so as to prevent fluid from leaking into or out of cavity 46.

The outer end of inclined bore 48 is threaded to receive a threaded end extension 64 of motor support housing 4. Disposed in motor support housing 4 is a reversible electric motor 66. The latter may be an a.c. or d.c. motor. The motor is secured in place in housing 4 by a plurality of set screws 68 that are screwed into threaded holes in that housing. Other means may be used to hold the motor in place.

The output shaft 67 of motor 66 carries a worm gear 78 which is sized and positioned to mesh with pinion gear 56. The electric terminals of the motor are connected at 70 to an electric cable 72 that is captivated in an insulator end cap 74 that is screwed into or otherwise secured in a threaded opening 76 in the outer end wall of motor support housing 4. Cable 72 is connected to a power supply (not shown) via a suitable switch means (not shown) that is adapted to activate motor 66 and also cause it to selectively operate in a forward or reverse direction. By way of example, the switch means may be mounted to motor support housing 4 or to housing 2. Also by way of example, the switch means may take the form of a foot-operated switch connected into the electric power circuit for the motor, so as to leave the surgeon's hands free to manipulate the endoscope to which the invention is attached or to conduct other procedures.

The adaptor 38 is used in attaching a video camera head, such as that shown in phantom at 80 in FIG. 7, to housing 2. As seen in FIG. 4, adaptor 38 is a cap-like element including a first hollow, internally threaded, cylindrical portion 82 that is sized so that it can be screwed onto the externally threaded portion 36 of the proximal end of housing 2. Portion 82 includes an internal distally-facing annular shoulder 84 that engages O-ring sealing member 44 when adaptor 38 is screwed onto housing 2. Adaptor 38 also includes a second hollow cylindrical portion 86 with a smaller outer diameter than the outer diameter of portion 82. The outer surface of portion 86 is formed with screw threads 88 whereby a camera head 80 can be screwed onto adaptor 38 (see FIG. 7). The proximal end of adaptor portion 86 has a stepped inner surface forming a flange 90 that serves on one side as a shoulder against which a second transparent window 92 is or may be secured hermetically by a suitable fluid-impermeable cement. Preferably, the smallest inner diameter of adaptor 38 (exclusive of flange 90) is approximately the same as the inner diameter of shoulder 14, so that its shoulder 84 can act as a proximal mechanical travel stop for a lens transport assembly 100 (FIG. 4). Adaptor 38 may be provided with several blind holes (not shown) for accepting a spanner wrench (also not shown) to facilitate screwing the adaptor onto and off of housing 2.

Lens transport assembly 100 is slidably disposed in bore 10. The lens transport assembly comprises a focusing lens set that is disposed in and fixed to a hollow cylindrical lens set carrier 102. In the illustrated embodiment the lens set comprises four lenses 104, 106, 108 and 110, with lenses 104, 106 being spaced from lenses 108, 110. It should be noted that the number, configurations and spacing of the lenses in the lens set is not critical to the invention. Lenses 104–110 are shaped to sharply focus the beam passed by the endoscope onto the image plane of an attached camera, e.g., camera head 80. If a conventional optical endoscope 32 is attached to the focusing device, and if then the endoscope is positioned at its nominal (designed) object distance, the image beam passing out of the proximal (rear) end of the endoscope will be collimated, in which case the lenses 104–110 serve to focus the image beam onto the image plane of an attached camera 80. The lenses are preferably designed so that a collimated beam from the endoscope is sharply focused on the camera plane when the lens transport assembly 100 is approximately equidistant from the opposite ends of bore 10. If the endoscope is disposed at some other object distance, then the beam passed by the endoscope will either converge or diverge according to the particular object distance. Lenses 104–110 are shaped to focus the beam passed by the endoscope onto the image plane of the camera over a wide range of object distances, i.e., the lenses are capable of dealing with significantly converging and significantly diverging image beams. Since magnification and fields of view (which are related inversely to each other) are dependent upon the object distance, the present invention enables the surgeon to view a sharply focused image over a wide range of magnifications and fields of view resulting from changes in object distance. The lens carrier has a diameter only slightly smaller than the diameter of bore 10, so as to make a close sliding fit in housing 2.

A mechanical biasing means is provided for the lens transport assembly 100. In the illustrated embodiment, the biasing means is a coil spring 112 (FIG. 4) disposed in bore 10. One end of the spring 112 engages shoulder 14, while its other end engages the adjacent annular distal end surface 114 of lens carrier 102. Spring 112 urges lens transport assembly 100 away from shoulder 14 toward the proximal end of housing 2. The distal-most position of lens transport assembly 100, i.e., the limit of movement away from shoulder 84, is that where spring 112 is substantially fully compressed. The proximal-most position of lens transport assembly 100, i.e., the limit of movement away from shoulder 14, is that where the annular proximal end surface 116 of lens carrier 102 engages shoulder 84 of adaptor 38.

The outer surface of lens carrier 102 is formed with a gear rack consisting of a series of gear teeth 118 that are engaged by the teeth of pinion gear 56. In the drawings the gear rack is in the six o'clock position on the lens carrier body. The gear teeth 118 are sized to mesh closely with the teeth of pinion gear 56 so that rotation of gear 56 will cause the lens transport assembly 100 to move axially in bore 10 with a minimum of hysteresis or backlash. Typically, this close meshing of gear teeth will be sufficient to maintain the orientation of the lens carrier so that its gear teeth 118 will always face cavity 46. However, if desired or necessary, a specific alignment-retaining means (not shown), such as a key projecting from lens carrier 102 into a longitudinal keyway in the side wall of bore 10 or vice versa, may be provided to prevent rotation of the lens carrier in bore 10 while allowing it to move longitudinally in that bore.

As is believed obvious from the foregoing description, the lens transport assembly 100 can be selectively moved in one direction or the other in bore 10 by operation of motor 66. The rotational movement of worm gear 78 by operation of motor 66 acts through pinion gear 50 and gear rack teeth 118 to cause longitudinal movement of lens transport assembly 100 in bore 10. Further, pinion gear 56 is restrained axially at one end by its contact with the side wall portion 59 of body 2 that forms the closed end of cavity 46. At its other end, pinion gear 56 is axially restrained by its sliding contact with the inner face of threaded plug 52. Sufficient clearance exists between pinion gear 56 and adjacent surfaces to ensure that the pinion gear can rotate freely in cavity 46, except as restrained by worm gear 78 or gear teeth 118.

Preferably, threaded plug 52 is provided with a screwdriver slot 53 (FIG. 7) to facilitate screwing it into and out of housing 2. Pinion gear 56 has a threaded axial hole 54 to facilitate its removal from the housing by pulling manually on a screw (not shown) that is screwed into hole 54. This combination of features is advantageous in that it facilitates removal of gear 56, thereby freeing the lens carrier 102 so that the lens transport assembly 100 can be removed from housing 2 upon removal of adapter 38. Removal of gear 56 also assures that the worm gear 78 is free for detachment of motor support housing 4.

As noted above, motor 66 may be operated to rotate gear 56 in either a clockwise or a counterclockwise direction, causing the lens carrier assembly to move proximally toward shoulder 84 or distally toward shoulder 14. With a preferred embodiment as shown in FIGS. 1–8, it has been found that a motor speed/gearing ratio arrangement which results in a longitudinal movement of lens transport assembly 100 of about 12 mm in about 3 seconds is satisfactory.

Figure 6:
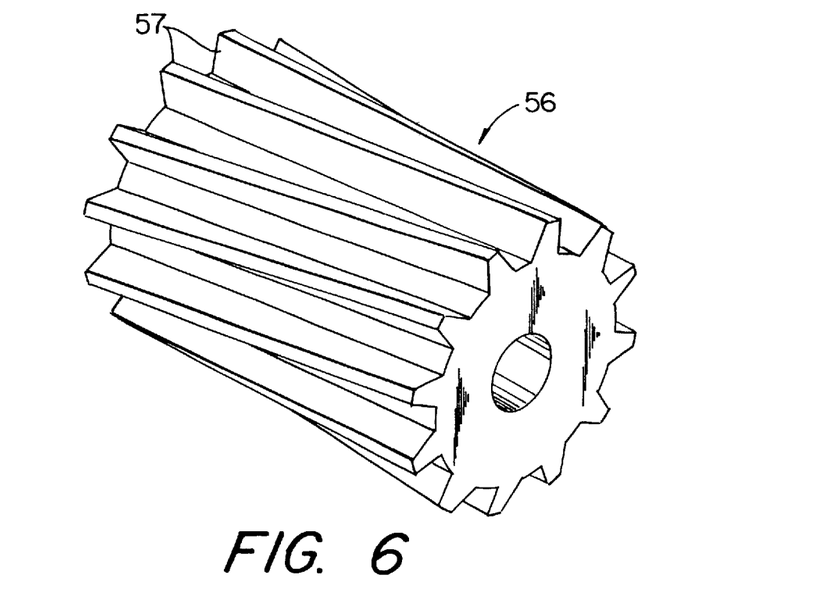
FIG. 6 is an enlarged perspective view of a helical pinion gear in accordance with the present invention and representatively shown in FIGS. 1–5.

Two additional features of the invention shown in FIGS. 1–7 also are to be noted. First, rack gear teeth 118 are preferably formed at an angle to the longitudinal axis of lens set carrier 102 and bore 10 which precisely matches the lead angle of the worm gear's teeth (typically about 3.5 degrees), and, as shown in FIG. 6, the gear teeth 57 of pinion gear 56 are formed with the same lead angle. This results in pinion gear 56 being a helical gear as shown in FIG. 6. In this regard, it is recognized that according to customary practice a worm gear normally nestles in a partially enveloping groove in the gear with which it mates, and that the profiles of the worm gear teeth and the pinion gear teeth differ somewhat. Nevertheless, in this case the dimensional differences are so slight as to assure satisfactory operation of the coupler.

Second, it is necessary to provide some clearance (backlash) between the meshing gear teeth so as to accommodate the tolerances of the manufacturing process. Such backlash may tend to cause a time delay (hysteresis) between the motion reversal of the drive output shaft of motor 66 and the consequent reversal of the direction of movement of the lens transport assembly 100 in bore 10. The spring 112 substantially eliminates this time delay. Specifically, the spring 112 urges the lens transport assembly 100 proximally in bore 10, thereby urging the pinion gear 56 to rotate so that rotation is arrested by engagement of the pinion gears teeth with the worm gear's teeth. Since the worm gear 78 is fixed relative to the motor output shaft, this configuration is maintained at all times due to the unceasing force of spring 112 against the distal end of lens transport assembly 100, with the result that backlash anywhere in the gear train is avoided. To elaborate, the lead angle of the teeth of worm gear 78 is so small that it is effectively a self-locking gear, and the forces initiated by spring 112, reflected back through the gear train described above, are insufficient to cause the motor output shaft to rotate against the driving force of motor 66.

Figure 8:
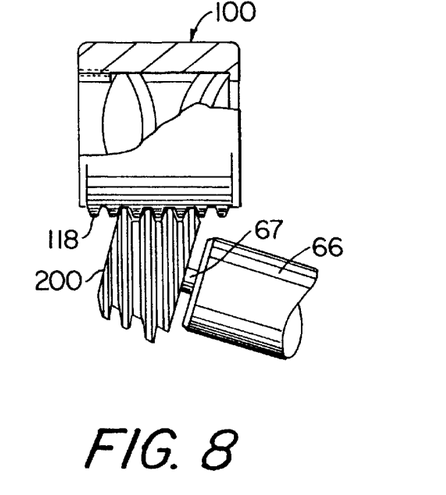
FIG. 8 relates to a modified form of the invention and is a side elevational view showing use of a conical spiral worm gear engaged with the rack gear teeth on the lens carrier.
Figure 9:
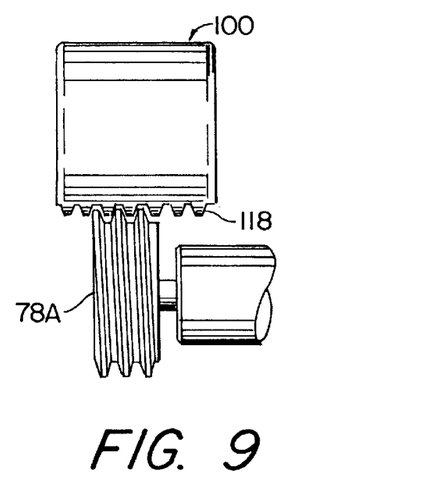
FIG. 9 relates to another modification of the invention and is a side elevational view showing a worm gear in engagement with the rack gear teeth on the lens carrier.

Alternative gear trains are also contemplated as representatively shown in FIGS. 8 and 9. These gear trains eliminate the pinion gear 56.

The gear train shown in FIG. 8 includes a conical spiral gear 200 coaxially affixed to the free end of the output drive shaft 67 of motor 66. The teeth of the conical spiral gear 200 extend into housing 2 and mesh directly with the rack gear teeth 118 of lens transport assembly 100. Accordingly, aside from a reconfiguration of housing 2, the elimination of pinion gear 56 and the substitution of conical spiral gear 200 for worm gear 78, this alternative is substantially the same as the device described in detail above.

The second alternative gear train shown in FIG. 9 is perhaps the simplest, although not the most compact. As in FIG. 8, the pinion gear 56 is eliminated, and a conventional worm gear 78A is substituted for worm gear 78. Also in this case the worm gear 78A is mounted so that its axis is parallel to the longitudinal axis of bore 10. In this case, the diameter of worm gear 78A needs to be substantially larger than that of motor 66 in order to avoid any mechanical interference with adaptor 38.

Although not shown, it is to be understood that motor housing 4 or housing 2 could be provided with manually-operated switch means for causing the motor 66 to operate in the forward or reverse direction as desired.

Figure 10:
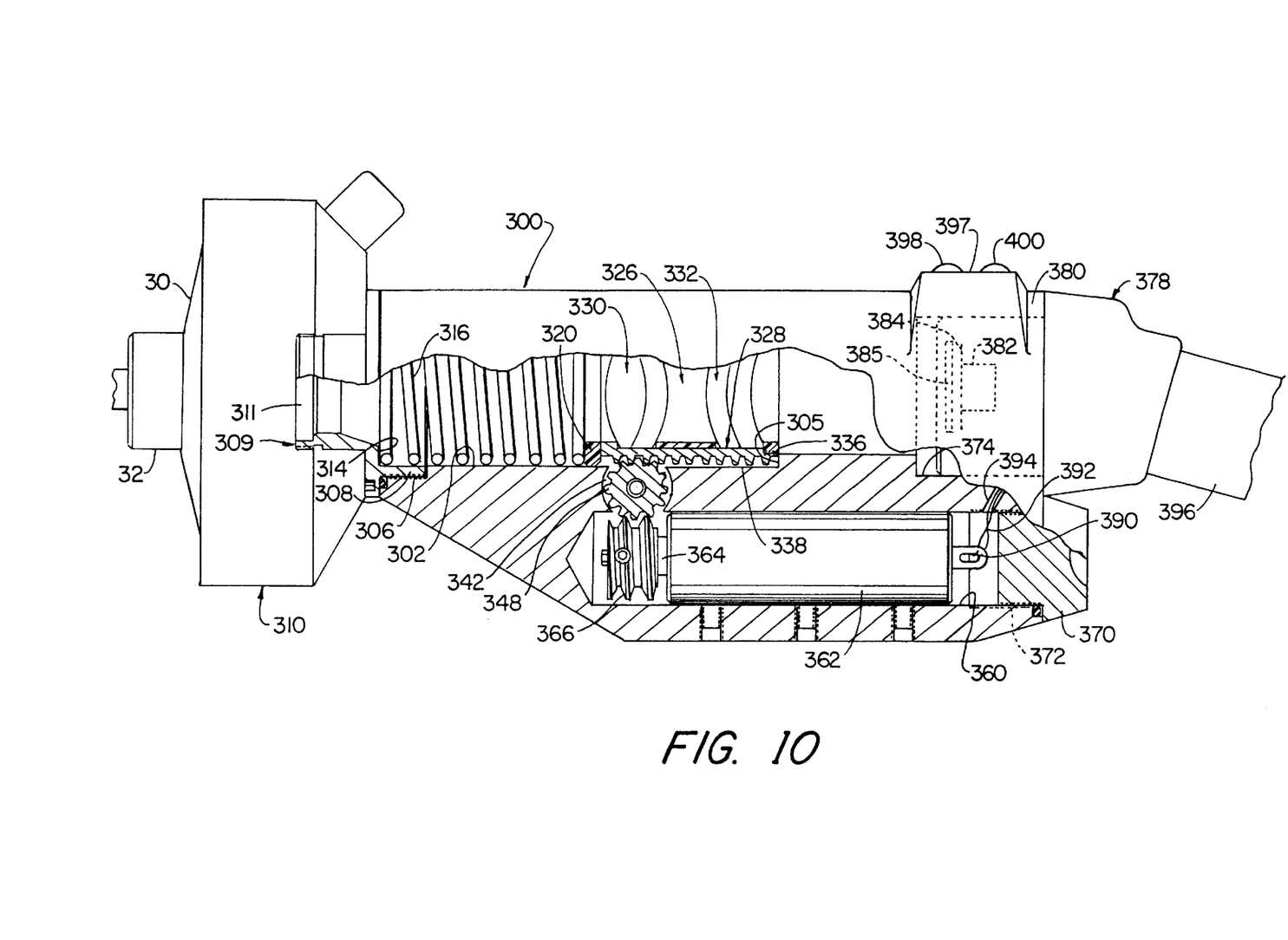
FIG. 10 relates to another form of the invention and is a left side elevational view, partly in section, showing a conventional optical endoscope and coupler attached thereto.
Figure 11:
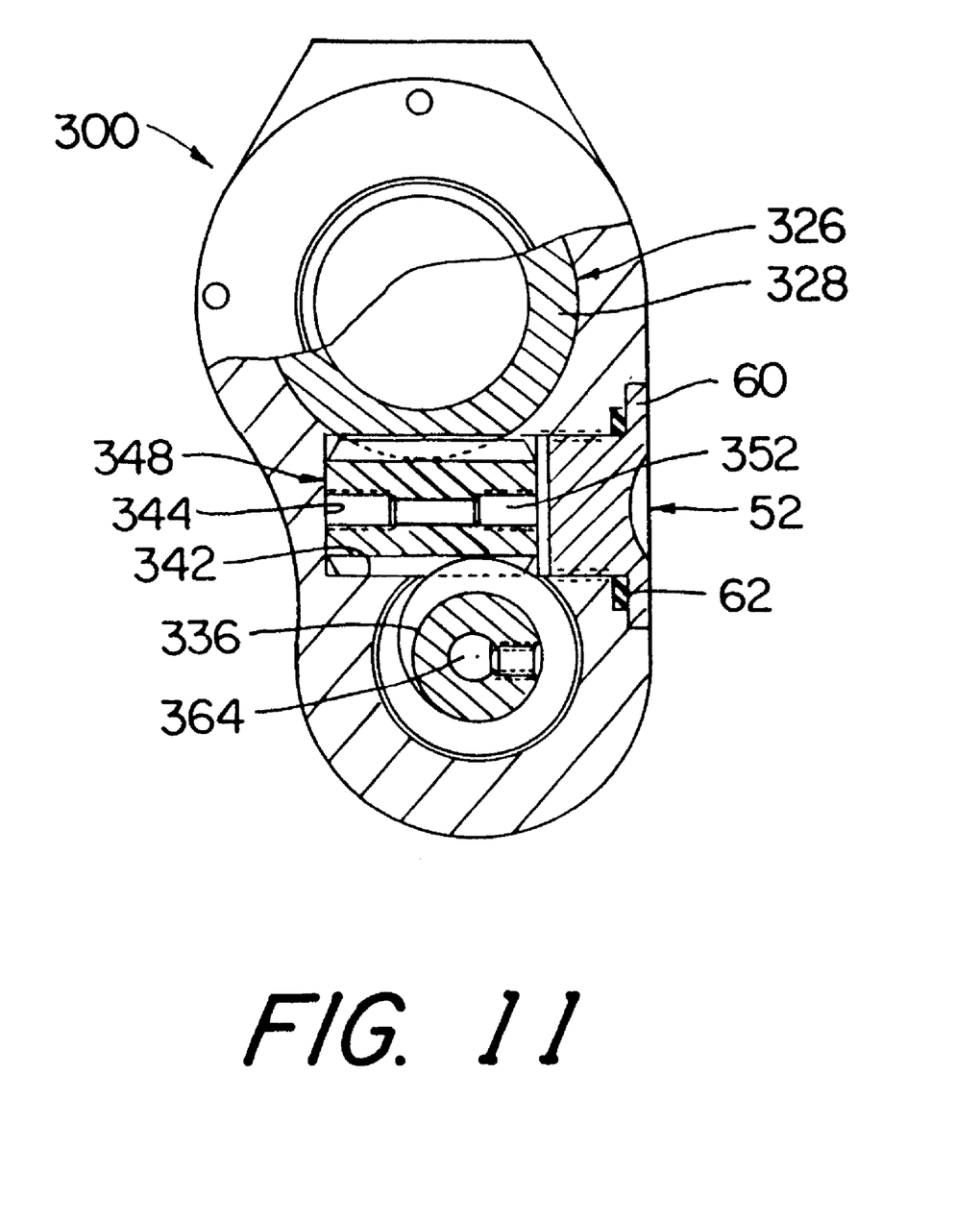
FIG. 11 is a proximal end view of the viewing system of FIG. 10, partially cut away through the axis of pinion gear 348.

Turning finally to FIGS. 10 and 11, an endoscopic viewing system suitable for use with many different endoscopes is shown. In essence, this system combines a motorized focusing coupler similar to the one just described with a video camera in a single housing. The convenience of this combination cannot be overstated. As alluded to above there are many different types of conventional optical endoscopes designed for many different and particular uses. However, the viewing devices at the proximal end of all optical endoscopes are very similar. Substantially most, if not all, conventional optical endoscopes have eyepieces or viewing devices that provide a collimated image beam output, i.e., focused substantially to infinity. The integrated focusing device/video camera arrangement illustrated in FIGS. 10 and 11 consolidates the apparatus which needs to be provided to convert an optical endoscope to a video endoscope.

The embodiment shown representatively in FIGS. 10 and 11 includes a housing 300 having a cylindrical bore 302. The bore 302 is reduced in diameter at 304 so as to form a shoulder 305 at the opposite end of the housing. The diameter at the distal end of bore 302 is enlarged to form a cylindrical surface which is provided with internal threads 306 for mating with an externally threaded proximal end extension 308 of an adaptor 309 which is adapted to be releasably attached to a conventional endoscope coupler 310. In the specific embodiment of FIG. 10, the distal (front) end of adaptor 309 is externally threaded for making a screw connection to coupler 310. However, adaptor 309 may be provided with some other means, e.g., a bayonet type lock, for attaching it to an endoscope coupler as shown at 310. The forward end of adaptor 309 is hermetically closed off by a window 311. The adaptor 309 has an internal annular shoulder 314 which acts as a stop or retainer for a spring 316. The opposite end of spring 316 is engaged with an insulator ring 320 that in turn is engaged with the distal end surface of a lens set carrier 328 which forms part of a lens transport assembly 326. Spring 316 urges the lens transport assembly toward shoulder 306, and the latter acts as a proximal limit stop for lens set carrier 328. Mounted within the carrier 328 are two lens sets 330 and 332 which are shaped so as to serve as focusing lenses. The lens set 332 is spaced from the lens set 330 by an internal cylindrical spacer. The number, configuration and spacing of the lens mounted to carrier 328 are not critical to the invention. The proximal end of the lens set carrier 328 is internally threaded to receive an externally-threaded retainer ring 336 which acts to keep the two lens sets fixed in carrier 328. As seen in FIG. 10, the lens carrier 328 is formed with a gear rack comprising a plurality of teeth 338 which are arranged in series lengthwise of the carrier at approximately the six o'clock position.

Housing 300 also has a second bore 342 (FIG. 11) which extends at a right angle to the axis of bore 302. Bore 342 intersects bore 302, as shown in FIGS. 10 and 11. Bore 342 is essentially a blind hole, the inner end having a flat end surface 344 which forms part of the wall of housing 300. The outer end of bore 342 is internally threaded to receive a threaded plug member 52. The latter has a flange 60 which engages an O-ring seal 62 that is seated in a groove in housing 300. Flange 60 also is seated in a groove in housing 300 as shown in FIG. 11. A pinion gear 348 makes a close rotating fit in bore 342, with the gap between the gear and the surrounding portion of housing 300 being such as to allow the gear to rotate freely in bore 342. When the plug 52 is fully screwed into bore 342, a slight gap exists between pinion gear 348 and the flat surface 344, so as to assure that pinion gear 348 will not be bound between that surface and the main portion of plug 52. Pinion gear 348 is engaged with rack gear teeth 338. Like pinion gear 56, gear 348 has a threaded center hole 352 to accommodate an externally threaded tool (not shown) that is used to remove that gear from bore 342.

A third bore 360 is also formed in the housing 300. This third bore 360 extends parallel to bore 302 and intersects bore 342 at approximately the six o'clock position. The bore 360 is essentially a blind hole, with the hole being open at the proximal end of body 302. Mounted within bore 360 is a reversible electric motor 362 that is like motor 66 and has an output drive shaft 364 on which is secured a worm gear 366. The latter is engaged with the teeth of pinion gear 348, so that when motor 362 is energized to cause rotation of worm gear 366, pinion gear 348 will be caused to rotate in a direction determined by rotation of the worm gear, and such rotation of gear 348 will cause the lens transport assembly to move in one direction or the other according to the direction of rotation of the worm gear. Movement of the lens transport assembly is urged in one direction by spring 316, but will not occur unless motor 362 is operated so as to rotate the worm gear 366. The self-locking nature of the worm gearing is such that when the motor is shut off, the lens transport assembly will be stationary despite the biasing force exerted by spring 316. The purpose of the spring is to substantially eliminate any hysteresis or backlash affecting the lens transport assembly. The outer end of bore 360 is closed off by a plug 370, the plug being externally threaded so as to make a screw connection with internal threads 372 at the outer end of bore 360.

The proximal end of bore 302 is counterbored as shown at 374 for the purpose of accommodating the forward section 380 of a video camera head 378. The camera head is secured to housing 300 by suitable means, e.g., by screw threads (not shown). The distal end of the forward section 380 of the video camera head is in axial alignment with bore 302 and contains a solid state imaging device, preferably in the form of a CCD, illustrated schematically in phantom at 382, with the image plane of the CCD being indicated by the line 384. A window 385 in the forward section 380 hermetically protects the solid state imaging device.

The output terminals 390 of motor 362 are connected by wiring illustrated at 392 which leads to the interior of the camera head via a passageway 394 in housing 302 that intersects the proximal counter-bored end 374 of bore 302. The camera head has a cable 396 which contains conductors for operating the CCD 382 and recovering output signals from that imaging device, plus conductors connected to wiring 392 for powering the motor.

The apparatus shown in FIGS. 10 and 11 further includes a protuberance 397 on the housing 300, and mounted in that protuberance are two push-button switches 398 and 400. The latter are connected to the power circuit for motor 362, with the push-button switch 398 when closed serving to energize the motor in a forward direction, and the switch 400 when closed serving to energize the motor in the reverse direction. Additional switch means may be incorporated into housing 300 or camera head 378 for the purpose of providing manual control of the camera operating circuits. Also, the power circuits for motor 362 may be connected to foot-operated switch means (not shown), so as to allow foot control while leaving the surgeon's hands free to manipulate the endoscope or conduct other procedures.

The arrangement shown in FIGS. 10 and 11 offers the advantage that the endoscope 32 may be quickly released from the coupler 310 according to conventional practice, and such disconnection of the endoscope 32 from the coupler leaves the remaining apparatus intact. Also, a different coupler may be substituted easily for coupler 310, since the latter can be detached from adaptor 309 by a simple unscrewing action. A further advantage is that by unscrewing the adaptor 309, it is possible to remove the spring 316 for the purpose of replacing or inspecting the lens transport assembly. The arrangement of FIGS. 10 and 11 also eliminates the need for a proximal seal or a transparent window between the focusing device and the camera head. Further, the power supply for the motor 362 may be integrated into the electronic circuitry of the camera so as to further simplify the overall apparatus.

With a system as illustrated in FIGS. 1–7 or 10–11, a surgeon is able to precisely focus the image captured by an endoscope onto the image focal plane of a camera over a relatively wide range of object distances, characterized by substantial changes in magnification and fields of view. Operation of the focusing coupler is straightforward. If the captured image displayed by the display device is not in focus or if the surgeon wishes to change magnification and fields of view by increasing or decreasing the object distance, the surgeon activates and controls operation of motor 66 or 362 so as to cause its output shaft to rotate in the "forward" or "reverse" drive mode as required to cause the lens transport assembly to move in a direction that will bring the displayed image into sharp focus. Movement of the lens transport assembly in response to drive shaft rotation occurs rapidly with minimal hysteresis because the spring force exerted on the lens transport assembly removes substantially all backlash from the gear train. The amount and speed of movement of the lens transport assembly will depend upon the motor speed and the gearing. The gearing parameters are selected to permit the lens transport assembly to be moved precisely in small increments so as to facilitate sharp focusing.

It also should be appreciated by those skilled in the art that the coupler device of the present invention and the display system used to view the images provided by use of the present invention may be permanently installed into an operating room. With such an installation, the surgeon need only attach the viewing end of his endoscope of choice to the focusing device already present in the room, and actuate the display system and the camera, in order to be able to have a clear image of the operative site displayed by means of a TV monitor or head-mounted display device.

It is within the contemplation of the present invention that any well known apparatus for operating a reversible motor may be used in association with the present invention. It also is contemplated that the apparatus may be combined with an autofocus system (not shown) which is capable of automatically maintaining the image viewed by the surgeon in sharp focus. For example, autofocus systems are known which electrically sample the output image quality and provide control signals which operate a motor drive, so as to adjust the position of a focusing lens unit in a direction to ensure the presentation of the sharpest image possible with the available optical system. Other autofocus systems which measure object distance may be used to control operation of the focusing device.

The invention herein described has numerous advantages. The focusing coupler devices of FIGS. 1–11 are sterilizable, easily, repeatedly and efficiently. Also, while the illustrated devices may be made as integral sealed units, the ability to remove the lens transport assemblies for repair or replacement is an important advantage. A further advantage is that the focusing coupler device is driven by an internal electromechanical drive system, and hence free of "bug traps" typical of manual focusing devices.

Although specific forms of an endoscope focusing coupler device and a system utilizing the same have been described and illustrated herein, it is to be understood that such have been disclosed by way of illustration, rather than by way of limitation. Those skilled in the art will realize from the foregoing specification that a focusing device wherein the lens assembly is internally electromechanically movable in a bore in a housing may be applied in numerous other optical contexts. Thus, for example, the focusing device or system described might be coupled to an optical image capturing device other than an endoscope. Also, it is contemplated that the focusing device need not necessarily be coupled to a video camera. Instead, it may be used for direct ocular viewing of an image presented by the endoscope. In the latter case, the focusing device serves to keep the image formed by the endoscope focused on the retina of the observer's eye(s) over a relatively large range of object distances, thereby making use of the endoscope less tiring on the surgeon.

It should be appreciated further that the invention is not limited to monocular systems, but may be applied to stereoscopic systems as well.

Also, the distal end extension of housing 2 could be modified so as to permit it to be coupled directly to the endoscope, thereby omitting the need for an endoscope holder.

Numerous other variations, alterations, modifications and changes to the above-described preferred embodiment of the present invention will occur to those skilled in the art in view of the foregoing detailed description of a preferred embodiment of the invention and the drawings appended hereto. Therefore, it will be understood that this specification and its appended drawings are to be considered as illustrative only, and not as limiting of the present invention in its broadest aspects. It is intended that the present invention be understood as being limited only by the terms of the appended claims.

What is claimed is:

1. A motorized focusing coupler device, said coupler device comprising:

a housing having a distal end and a proximal end and comprising (i) a first substantially straight bore having a distal end and a proximal end, (ii) first attaching means at said distal end of said housing for mechanically attaching said housing to an image capturing device, (iii) second attaching means at said proximal end of said housing for mechanically attaching said housing to an image receiving apparatus, (iv) a second bore in said housing, and (v) a cavity connecting said first and second bores;

a tubular lens carrier slidably disposed in said first bore for reciprocal movement along said first bore between a proximal-most position and a distal-most position, said lens carrier supporting at least one coaxially mounted focusing lens and a longitudinally-extending series of rack gear teeth; p1 a reversible electromechanical drive assembly mounted to said housing, said drive assembly having an output shaft extending into said second bore;

gear means connecting said output shaft to said series of rack gear teeth for selectively moving said lens carrier between its proximal-most and its distal-most positions in said bore in response to rotation of said output shaft, said gear means comprising a worm gear attached to said output shaft, and a helical pinion gear rotatably disposed in said cavity, with the teeth of said helical pinion gear in meshing engagement with the teeth of said worm gear and said rack gear teeth; whereby an image captured by said image capturing device and relayed by said at least one focusing lens may be focused on an image receiving device by movement of said lens carrier.

2. A motorized focusing coupler device according to claim 1, wherein said second bore extends parallel to said first bore.

* * * * *

UNITED STATES PATENT AND TRADEMARK OFFICE
CERTIFICATE OF CORRECTION

PATENT NO. : 6,292,221 B1
DATED : September 18, 2001
INVENTOR(S) : Philip R. Lichtman Page 1 of 1

It is certified that error appears in the above-identified patent and that said Letters Patent is hereby corrected as shown below:

<u>Column 13, claim 1,</u>
Line 3, delete "pl" and start a new paragraph with the words -- a reversible --.

Signed and Sealed this

Twenty-sixth Day of February, 2002

*Attest:*

JAMES E. ROGAN
*Director of the United States Patent and Trademark Office*

*Attesting Officer*